(12) United States Patent
Görz et al.

(10) Patent No.: US 11,071,605 B2
(45) Date of Patent: Jul. 27, 2021

(54) STERILIZING SCREEN TRAY COMPRISING A HANDLE THAT CAN BE SHIFTED INTO THE REMOVAL POSITION BY MEANS OF ACTUATION

(71) Applicant: Aesculap AG, Tuttlingen (DE)

(72) Inventors: Dennis Görz, Tuttlingen (DE); Bianca Rosin, Tuttlingen (DE); Eva Streit, Bodman-Ludwigshafen (DE); Timo Knittel, Wurmlingen (DE); Frank Weller, Scharbeutz (DE); Matthias Henke, Fridingen (DE)

(73) Assignee: AESCULAP AG, Tuttlingen (DE)

( * ) Notice: Subject to any disclaimer, the term of this patent is extended or adjusted under 35 U.S.C. 154(b) by 0 days.

(21) Appl. No.: 16/978,255

(22) PCT Filed: Mar. 1, 2019

(86) PCT No.: PCT/EP2019/055184
§ 371 (c)(1),
(2) Date: Sep. 4, 2020

(87) PCT Pub. No.: WO2019/170552
PCT Pub. Date: Sep. 12, 2019

(65) Prior Publication Data
US 2021/0000561 A1 Jan. 7, 2021

(30) Foreign Application Priority Data
Mar. 5, 2018 (DE) .................... 10 2018 104 942.0

(51) Int. Cl.
*A61B 50/34* (2016.01)
*A61B 50/33* (2016.01)
(Continued)

(52) U.S. Cl.
CPC .............. *A61B 50/34* (2016.02); *A61B 50/33* (2016.02); *B65D 25/2835* (2013.01); *A61B 2050/005* (2016.02); *A61B 2050/3011* (2016.02)

(58) Field of Classification Search
CPC ............ A61B 2050/3011; A61B 50/33; A61B 50/34; B65D 2525/288; B65D 2525/286; B65D 25/2852; B65D 25/2835
(Continued)

(56) References Cited

U.S. PATENT DOCUMENTS 3,572,870 A * 3/1971 Marks ................... A45C 13/22
312/244
5,005,255 A 4/1991 Pare et al.
(Continued)

FOREIGN PATENT DOCUMENTS

CN 202022390 U 11/2011
DE 2834474 A1 2/1980
(Continued)

OTHER PUBLICATIONS

Written Opinion of the International Searching Authority received in Application No. PCT/EP2019/055184 dated May 22, 2019, 10 pages.
(Continued)

*Primary Examiner* — Steven A. Reynolds

(57) ABSTRACT

A strainer dish for receiving medical items to be disinfected or sterilized includes a receiving container and at least one handle, which, in a removal position projects out of the receiving container in a grippable manner in order to allow the carrying of the strainer dish, and which, in a locking position, is arranged inside the receiving container to allow the loading of the strainer dish, the handle being shifted from the locking position into the removal position by actuation of a releasable holding element.

18 Claims, 3 Drawing Sheets

(51) Int. Cl.
*B65D 25/28* (2006.01)
*A61B 50/00* (2016.01)
*A61B 50/30* (2016.01)

(58) Field of Classification Search
USPC .................. 220/762, 763, 764, 769; 206/370
See application file for complete search history.

(56) References Cited

U.S. PATENT DOCUMENTS

| | | | |
|---|---|---|---|
| 5,281,400 A | 1/1994 | Berry, Jr. | |
| 2010/0320108 A1* | 12/2010 | Riedel | B25H 3/02 |
| | | | 206/372 |
| 2014/0216966 A1* | 8/2014 | Ramkhelawan | A61B 50/20 |
| | | | 206/370 |

FOREIGN PATENT DOCUMENTS

| | | |
|---|---|---|
| DE | 10101424 C1 | 6/2002 |
| DE | 102006062379 A1 | 6/2008 |
| DE | 202010005788 U1 | 9/2010 |

OTHER PUBLICATIONS

German Search Report received in Application No. 10 2018 104 942.0 dated Sep. 19, 2018, 18 pages. (with translation).
International Search Report received in Application No. PCT/EP2019/055184 dated May 22, 2019, 5 pages. (with translation).

* cited by examiner

STERILIZING SCREEN TRAY COMPRISING A HANDLE THAT CAN BE SHIFTED INTO THE REMOVAL POSITION BY MEANS OF ACTUATION

CROSS-REFERENCE TO RELATED APPLICATION(S)

This application is the United States national phase entry of International Application No. PCT/EP2019/055184, filed Mar. 1, 2019, which claims the benefit of priority of German Application No. 10 2018 104 942.0, filed Mar. 5, 2018. The contents of International Application No. PCT/EP2019/055184 and German Application No. 10 2018 104 942.0 are incorporated by reference herein in their entireties.

FIELD

The present invention relates to a sterilizing tray/strainer dish, also referred to as strainer basket/screen basket, such as a sterilizing or disinfecting strainer dish. Generic strainer dishes are used to provide a portable receiving container for a number of items to be disinfected or sterilized, such as surgical cutting or gripping instruments, in a cleansing or disinfecting apparatus (RDG) or autoclave in a processing unit for medical products (AEMP) or a central supply department for sterile items.

BACKGROUND

Strainer baskets are part of the instrument cycle and are repeatedly cyclically cleaned and packed with (e.g. surgical) instruments, before they are sterilized in sterilizing containers/sterile containers, for example, and from the AEMP are transported to an operating theater (OP).

Against this background, strainer dishes should be easy to transport and, resp., to handle and, consequently, should have handles. Said handles firstly should not or as little as possible impair/limit the packing volume spanned by the strainer dish. It is resulting herefrom that the handles of the strainer dishes should occupy as little as possible to no space at all in the interior of the strainer dish. Secondly, the handles should impede the process of loading and packing (with instruments) as little as possible, while they should at the same time be properly accessible for a user.

Finally, the handles thirdly should also be configured so that aseptic/sterile removal of the loaded instruments is possible in the OP in a preferably ergonomic manner.

From DE 000010101424 C1 a strainer dish having a locking/folding handle is known. Said handle may adopt a removal position at which it projects from the interior of the strainer dish to be conveniently grippable in order to allow carrying of the strainer dish between the individual stations of the cycle thereof. Moreover, the handle can adopt a locking position in which loading of the strainer dish is possible. DE 000010101424 C1 already deals with the challenge of easily reaching the handle in the removal position and storing the same in the locking position in a most space-saving manner in the interior.

It is a drawback of the locking/folding handle known from prior art that the handle or handles in the locking position project deeply into the interior so that the space occupied by them in the interior cannot be occupied by items/instruments to be loaded any more. The loading volume of the strainer dish is thus reduced.

Moreover, said locking/folding handles show the drawback that, in the case of aseptic removal when as few surfaces of the strainer dish are to be contacted with the environment, they have to be passed out of the strainer dish in a very unhandy, i.e. "non-ergonomic" manner and can be shifted from the locking position into the removal position with increased effort only: Either the handle has to be pulled up by a user's thumb (which may easily result in the handle getting out of place) or the hands have to be turned so that the palm of the hand faces outwardly/laterally (which is not ergonomic).

It is another drawback of the locking/folding handles that, when the locking handles are pulled upwards, they can inadvertently entrain instruments with which the strainer dish is loaded so that said instruments are lifted and possibly will even be damaged and/or stained.

SUMMARY

In view of this prior art, the object underlying the present invention is to eliminate or at least to alleviate the drawbacks from prior art and especially to provide a strainer dish which includes such handles which, on the one hand, in the AEMP occupy as little space as possible (up to no space at all) in the interior of the strainer dish and impair the packing process/the loading with instruments as little as possible (up to not at all). On the other hand, such handle is to be provided which in the OP allows ergonomic aseptic shifting from the locking position into the removal position without any (great) additional effort and, accordingly, also ensures ergonomic aseptic removal of the strainer dish from the sterilizing container.

The basic idea and the functional concept of the present invention substantially consists in dividing the afore-described shifting operation previously carried out completely manually for shifting/transferring the handle and the holding/gripping bracket thereof from its locking position into the removal position according to the foregoing definition functionally and preferably structurally into a manually actuatable holding/gripping bracket release function and a subsequent automatically actuated shifting function. Said functional and, where appropriate, structural division of the entire shifting operation basically allows to arrange the handle and, resp., the holding/gripping bracket thereof on the strainer dish in an uncompromisingly space-saving manner so that, when it adopts its locking position, it can no longer or only with difficulty be directly reached/actuated by hand. Instead, according to the invention, a separate release/actuating mechanism (in addition to the holding/gripping bracket) is arranged on the strainer dish to be freely accessible from outside of the strainer dish, which release/actuating mechanism is merely provided and designed for holding the holding/gripping bracket in its locking position and for releasing the holding/gripping bracket upon manual actuation thereof. Moreover, the handle is provided with or, resp., is assigned to a drive mechanism which is provided and designed for automatically transferring the holding/gripping bracket thereof from its locking position into its removal position (after having actuated the holding/gripping bracket thereof manually for release).

Thus, the following further advantages, for example, can be derived from this configuration of a strainer dish according to the invention:

The handles and, resp., the holding/gripping brackets thereof can be arranged almost arbitrarily such that they take an as space-saving locking position as possible which will have no/little effect on the obtainable degree of compactness of the loading and, resp., will retain the almost maximum loading volume.

Removal of the strainer dish from the sterilizing container is possible in a time-efficient and intuitive manner, as no longer the handle or the holding/gripping bracket thereof itself has to be directly actuated manually, but merely a release/actuating mechanism provided separately herefrom and acting on the holding/gripping bracket to has to be actuated.

The loaded instruments are prevented from getting out of place or even from being damaged when shifting the handle and, resp., the holding/gripping bracket thereof from the locking position into the removal position.

Robust carrying and moving of the strainer dish is possible by stably mounted handles.

The subject matter of the invention therefore is a strainer dish for receiving medical items to be disinfected or sterilized (in general: to be cleaned), comprising a receiving container and at least one handle and, resp., the holding/gripping bracket thereof mounted/rotatably arranged therein which, in a removal position, projects from the receiving container in a graspable manner in order to allow carrying of the strainer dish, for example for removal from a sterilizing container, and which, in a locking position, is arranged preferably completely or at least substantially completely inside the receiving container and/or close to the container wall thereof in order to allow free unobstructed loading/unloading of the strainer dish or else transporting of the strainer dish inside the sterilizing container.

According to the invention, the handle is or can be shifted from the locking position to the removal position by means of actuation of a reachable and manually releasable holding element of the release/actuating mechanism by the then impacting drive mechanism in a preferably biased, especially spring-biased manner. In this way, the manually releasable holding element can be actuated by a user in a first step (as it can be reached/is accessible from the outer side of the strainer dish/from outside), before, triggered/initiated by said first step, in a second step the handle is moved by the drive mechanism from a position preferably inside the strainer dish, i.e. from the locking position, into a position accessible from outside, i.e. into the removal position. The mechanism incorporates a sophisticated technology.

Thus, it is possible that the invention meets the two (seemingly contrary) requirements of improved portability and optimized utilization of the interior, each per se and thus in a synergistic manner.

In other words, the invention can be functionally described so that on the strainer dish a manually releasable holding element is attached the actuation of which allows subsequent automatic shifting of the handle from the locking position into the removal position. Said automatic system (drive mechanism) is effectuated, of preference, by a spring the bias of which is released by actuating the holding element. Instead of manual pivoting according to prior art, with the strainer dish according to the invention a user merely has to perform e.g. a push-pull movement on the holding element, for example a bolt, pawl, claw etc., to extend/swivel out the holding bracket of the handle and to conveniently remove the strainer dish from the sterilizing container. Especially preferred, as it is both convenient to the user and space-saving, is the push-to-open system/push-to-open mechanism described in the following.

In an advantageous embodiment, at least one leg spring is responsible for the shifting movement of the handle from the locking position into the removal position. Further preferred, on each joint of the handle that rotatably couples the gripping/holding bracket to the receiving container a leg spring (inherent to the handle) is disposed so that for each handle two springs are used which ensure a robust guiding/robust automatic system of the handle/holding bracket in shifting from the locking position into the removal position. Leg springs excel by an inexpensive acquisition as well as a reliable operating mode and little space required.

Of preference, the receiving container of the strainer dish has a substantially rectangular basic shape (bottom plate) from which a box-shaped receiving container with flat (vertical) walls is resulting. Preferably, in the area of each of the two narrow/front sides of the basic shape/at each of the two narrow (vertical) walls of the box-shaped receiving container a bracket-type handle (made from a flat steel or aluminum belt) is arranged which extends over the entire front side. Said belt-type wide configuration (i.e. extending over the almost entire narrow container side) of the handle allows stable carrying/removal of the strainer dish. Further, in this embodiment, in the wide sidewalls (i.e. not in the narrow sidewalls) opposing joints/bearings for the bracket-type handle are provided close to the narrow sidewalls, which further promotes a space-saving arrangement of the handles.

In this embodiment, further advantageously in the locking position the bracket-type handles are arranged, preferably (approximately) free from slits, along the narrow sidewalls so that the volume of the interior of the receiving container to be reached by items is only reduced by the volume of the respective belt-type handle, which is minimal. In other words, the handle bracket adapts to the inner wall of the receiving container so that the handle bracket leaves no "dead volume", i.e. a volume that cannot be filled with items during loading. Hence, this has a favorable effect on the space available in the interior of the receiving volume.

Furthermore, in an advantageous development of said embodiment, the bracket-type handle which is preferably mounted in/on the wide sidewall is swiveled outwardly/laterally at least in longitudinal portions so that it is flush with or complementary to the narrow sidewall (front face) and, in the locking position, forms part of the inner wall of the receiving volume itself and, resp., stiffens the narrow sidewall. In this way, the handle in the removal position (as usual) adopts a handle function and moreover (according to the invention) in the locking position it adopts the limiting and/or stiffening function of an inner wall. Consequently, the volume of the receiving container is not reduced by the handle (apart from the mounting thereof), thus allowing maximum packing/loading.

When the handle adopts a limiting/stiffening function of the inner wall, on the surface facing the remaining inner wall preferably it has such a profile that a defined/centered abutment of the bracket against/on the inner wall is possible.

In a concrete advantageous development of the present invention, the strainer dish according to the invention includes two opposing narrow sidewalls (front faces) extending substantially vertically from a bottom plate and two opposing wide sidewalls (longitudinal faces) extending substantially vertically from a bottom plate which, together with the two narrow sidewalls and the bottom plate, define the maximum container receiving volume. At each of the end portions of the wide sidewalls facing the narrow sidewalls a handle bracket is mounted by pivot joints in which the biasing springs are accommodated/integrated which bias the handle brackets into the swiveled-out (removal) position thereof. The handle brackets are shaped and placed so that they extend in the swiveled-in (locking) position (substantially true to contours) along the respective assigned narrow sidewall and stiffen portions of the same and/or supplement/complete portions of the same so-to-speak as a substitute sidewall, i.e. form an efficient surface portion of the respective narrow sidewall. In/at each of the narrow sidewalls the releasable holding/release elements are spring-disposed, such as in the form of a spring-biased bolt or a spring-biased swivel claw, which hold the handle brackets in the swiveled-in locking positions thereof in a manually non-actuated state.

Another advantageous/alternative embodiment is characterized in that the releasable holding element is designed as a spring-biased movable detent lug/detent bolt, e.g. in the form of a slide. A slide is suited for reliably counteracting the bias of the handle that drives the same from the locking position to the removal position.

As an alternative to the movable detent lug, the releasable holding element is in the form of a spring-biased rotatable (rotary) disk. This enables a user to cause the shifting from the locking position into the removal position by means of intuitive rotation about few degrees against a bias, preferably about less than 10°.

Further alternatively to the detent lug or the rotary disk, the releasable holding element is designed as a pivotable clamping plate, such as in the form of a leaf spring. This offers the advantage that the required bias of the holding element is materialized by the holding element itself, which renders any additional spring component unnecessary.

In another advantageous configuration, the holding/release element to be actuated is a push-to-open mechanism. In such mechanism, by means of gentle pressure on the holding/release element the handle travels from the unlocking position to the removal position. To this end, when shifting the handle into the locking position, a spring of the holding/release element is biased and then is held in such a biased position that undesired re-opening is suppressed. If in the locking position pressure is exerted against the handle, the spring tensioned before is released and a pin shifts the handle into the removal position.

It is further especially advantageous when the releasable holding element of the strainer dish is arranged in the narrow container width direction, that is in the direction in which the handle extends or, resp., along the narrow front side, substantially in the center of the handle. In this way, the holding element can be easily reached and the force transmitted from the latter acts evenly on the handle.

In another advantageous embodiment, the strainer dish includes, apart from the receiving container and the handle mounted therein, a lid for safe transport of the strainer dish. The lid can be removed from the receiving container by actuating a lid release mechanism (i.e. when the lid release mechanism has been actuated, a form closure or force closure is released which allows the lid to be removed from the receiving container), wherein the actuation of the lid release mechanism simultaneously triggers the actuation of the releasable holding element. Thus, the handling of the straining dish is further facilitated: Only a lid release mechanism has to be actuated so that firstly the lid can be removed and secondly the handles are already found to be in the removal position.

In another embodiment including the lid, between the lid release mechanism and the releasable holding element a gear unit/a converting mechanism could be arranged for converting the movement resulting from the actuation of the lid release mechanism to a movement actuating the releasable holding element. Said additional converting mechanism establishes a direct and consequently robust connection between the lid and the releasable holding element.

In another advantageous configuration of the strainer dish according to the invention, the leg spring has a degressive characteristic line so that shifting from the locking position into the removal position takes place more quickly at the beginning than at the end of shifting. For a user this has the convenient effect that, after actuating the releasable holding element, he/she will directly observe a quick movement of the handle which then orderly closes into the removal position. Accordingly, it is possible, of preference, to provide an adjustable damping mechanism via which the movement characteristic of the handle can be adapted in the area of the handle.

BRIEF DESCRIPTION OF THE DRAWING FIGURES

In the following, the invention will be illustrated in detail by way of preferred example embodiments with reference to the accompanying figures. The figures are merely schematic and serve exclusively for the comprehension of the invention. Like elements are provided with like reference numerals, wherein.

DETAILED DESCRIPTION

Figure 1:
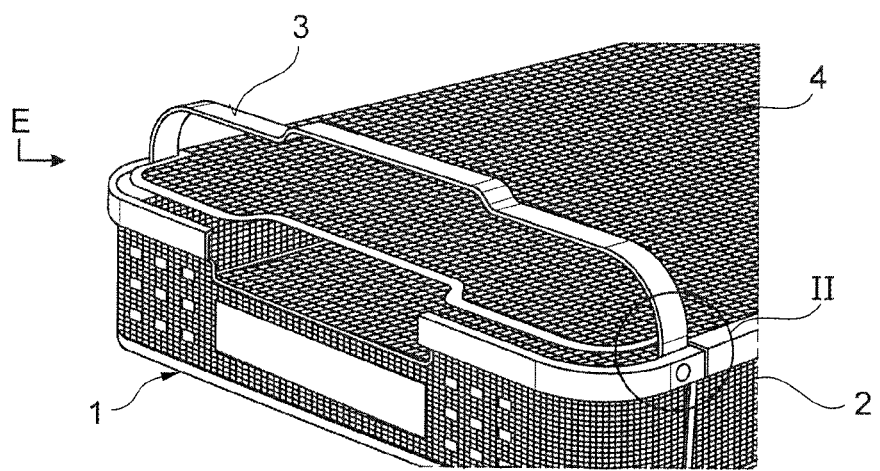
FIG. 1 shows a perspective view of a strainer dish according to the invention comprising a receiving container and a handle in a removal position as well as comprising a lid.

FIG. 1 generally represents a strainer dish 1 which is presently composed of a receiving container 2, at least one handle 3 and a lid 4. The strainer dish 1 and, resp., the handle 3 mounted thereon of FIG. 1 is in the removal position E, as can be seen from the projecting handle 3.

Figure 4:
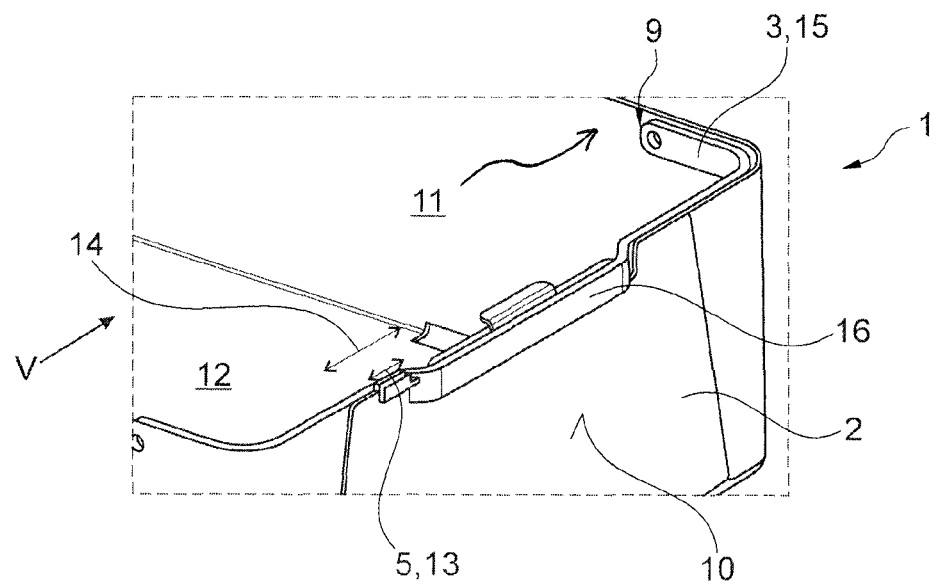
FIG. 4 shows a perspective view of a strainer dish according to the invention with the receiving container and the handle being in a locking position.
Figure 5:
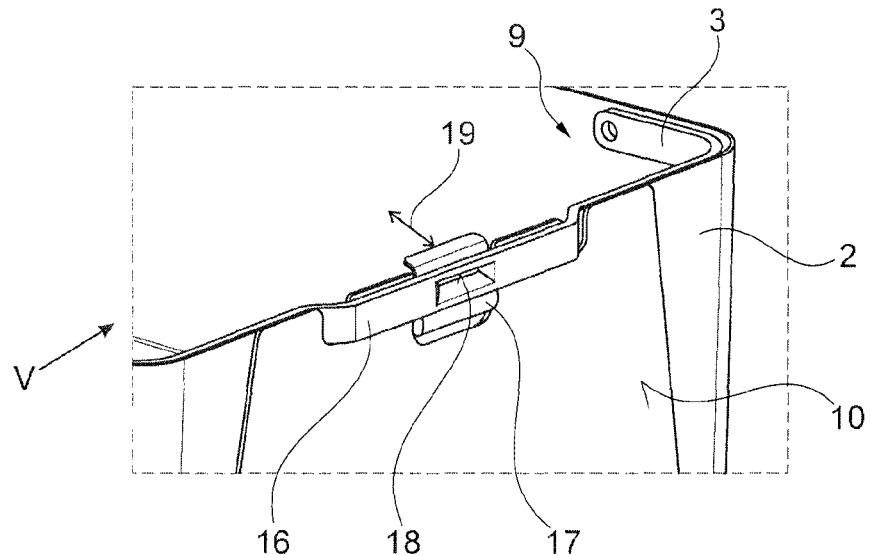
FIG. 5 shows a perspective view of a strainer dish according to the invention with the receiving container and the handle being in the locking position according to another embodiment.

According to the invention, the removal position, i.e. the preferred vertical projection of the handle 3 out of the receiving container 2, is caused automatically after appropriately actuating a releasable holding element 5 (not shown in FIG. 1, cf. FIG. 4 or 5). For this purpose, in the portion denoted with II in FIG. 1 a spring element urging the handle and, resp., the handle bracket 3 thereof into the (swiveled-out) (removal) position.

Figure 2:
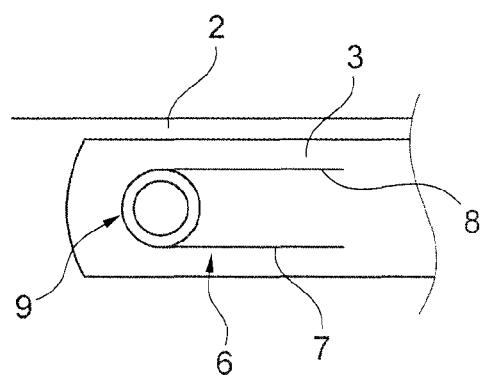
FIG. 2 shows a schematically illustrated leg spring (portion II of FIG. 1) in the locking position.

An exemplary embodiment of the spring element in portion II is schematically indicated in FIG. 2. Here a leg spring 6 including a fixed leg 7 and a moving leg 8 is interposed between the handle/handle bracket 3 and the receiving container 2. Said two legs 7, 8 are biased (as is common for a leg spring) against each other via a winding portion. Said bias reaches a maximum when the two legs extend in parallel to each other, as shown in FIG. 2.

As soon as the releasable holding element 5 is actuated by a user, it releases the handle bracket 3 in its locking position, whereupon the bias of the leg spring 6 shifts the handle/handle bracket 3 from a locking position V (cf. FIGS. 4 and 5) into the removal position E. During such transition/ shifting, the angle between the fixed leg 7 and the moving leg 8 is continuously increasing (and consequently the spring force is decreasing).

Figure 3:
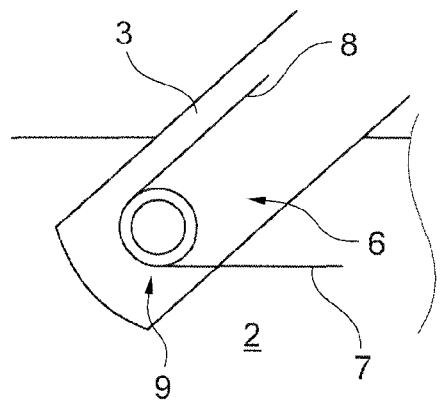
FIG. 3 shows the schematically illustrated leg spring of FIG. 2 when being shifted to the removal position.

As shown in FIG. 3, for example, the fixed leg 7 is retained in its position while the moving leg 8 travels away from the former.

The leg spring 6 is arranged, for example, in the area of a handle joint 9 of the handle according to the invention. The fixed leg 7 has to be coupled to the receiving container 2, while the moving leg 8 is tightly connected to the handle/handle bracket 3, so as to reliably shift the latter from the locking position V into the removal position E.

The solution according to the invention is not limited to the now illustrated leg spring. Instead, also other types of springs such as flexible springs, preferably leaf springs, spiral springs or e.g. torsion springs, preferably rod springs, coil springs, can be employed.

In FIG. 3, the moving leg 8 is rotated about approximately 45° from the fixed leg 7. In the final removal position E, the angle between the moving leg 8 and the fixed leg 7 is approximately 90°. This brings about optimum accessibility of the handle 3 in the removal position E. By a preferred degressive characteristic line of the leg spring 6, the first 45° are covered more quickly than the second 45°.

FIG. 4 illustrates the strainer dish 1 with the receiving container 2 and the handle/handle bracket 3 being in the locking position V. The handle 3 is bracket-shaped and extends complementarily to a front face/narrow sidewall 10 of the receiving container 2. The front face/narrow sidewall 10 forms, together with a lateral surface/wide sidewall 11 and a bottom 12 of the receiving container 2, the rectangular basic shape thereof.

In the locking position, the bracket-type handle 3 adapts to the associated front face 10 while making at least in portions abutting contact and is mounted in/on the lateral surface 11 by the handle joint 9. Consequently, the interior space of the receiving container 2 can be optimally utilized.

In FIG. 4, the releasable holding element 5 is a slide 13 movable in the direction of one of the lateral surfaces 11 which is mounted on an outer side of the front face 10. The slide 13 is spring-biased to be movable along the function line 14 which is oriented along/in parallel to the handle bracket 3 located in the locking position. The corresponding spring responsible for the spring bias is not shown in FIG. 4; it may be a simple helical compression spring, however. The handle/handle bracket 3 can be divided into a holding portion 15 and a gripping portion 16, the holding portion 15 extending at the two longitudinally spaced ends of the gripping portion 16 substantially at right angles and at its free end having a functional portion (e.g. a clearance hole) which is pivotally coupled to the joint 9. Moreover, in the gripping portion 16 of the gripping bracket 3 an undercut is formed/provided which is operatively engaged in the slide 13 in order to retain the handle bracket 3 in the locking position against the spring bias of the (leg) spring 6.

As soon as the slide 13 is moved away from the gripping portion 16, the form closure between the handle bracket 3 and, resp., the undercut formed thereon and the slide 13 will loosen so that the leg spring 6 disposed in the area of the handle joint 9 attains an automatic movement of the handle into the removal position E (cf. FIG. 1). As long as the slide 13 is in form closure with the handle 3/with the undercut, the handle 3 remains in the locking position V of FIG. 4. Hence, simple pushing of the slide 13 causes the shifting from the locking position V into the removal position E.

FIG. 5 illustrates an alternative embodiment of the manually releasable holding element 5. In this case, the releasable holding element 5 is in the form of a clamping plate 17. Said clamping plate 17 constitutes a leaf spring interacting with the gripping portion 16 of the handle bracket 3 due to the bias of the plate. To this end, in the gripping portion 16 a bulge or through-opening 18 is arranged/formed which enables a form closure to be formed between the clamping plate 17 and the gripping portion 16.

As soon as the clamping plate 17 is pressed away from the gripping portion 16 along its function line 19, the form closure between the handle bracket 3 and the clamping plate 17 will loosen so that the leg spring 6 disposed in the area of/inside the handle joint 9 attains the automatic movement of the handle into the removal position E (cf. FIG. 1). As long as the clamping plate 17 is in the form closure with the handle 3 caused by the bulge 18, the handle 3 remains in the locking position V of FIG. 5. Simple pressing of the clamping plate 17 thus causes shifting from the locking position V into the removal position E.

Figure 6:
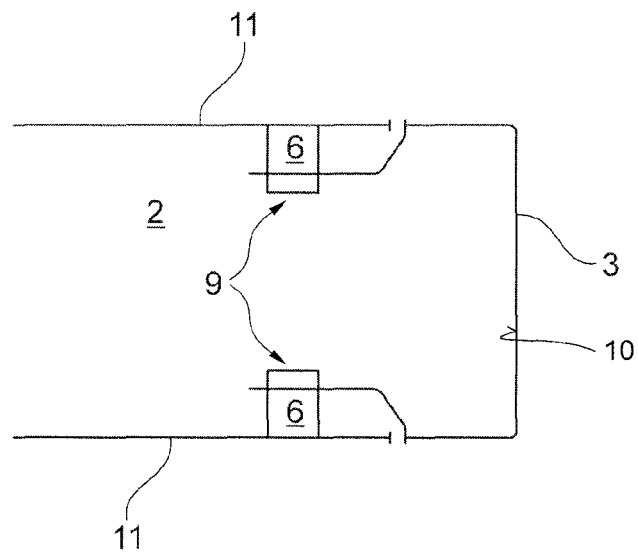
FIG. 6 shows another configuration of the handle.

In FIG. 6, another embodiment of the strainer dish 1 according to the invention is illustrated. The sidewalls 11 are schematically visible in the top view. The handle 3 is coupled to the receiving container 2 via the handle joint 9 or, resp., the handle joints in each of which a leg spring 6 is disposed.

According to the embodiment of FIG. 6, the handle 3 at least partially occupies the front face 11 of the strainer dish 1. This is made possible by the handle 3 swiveling outwardly away from the interior of the receiving container 2 after being linked to the handle joint 9. The inner volume of the receiving container 2 accessible for items/instruments is maximized in this way.

The invention claimed is:

1. A sieve basket for receiving medical articles to be disinfected or sterilized, having a receiving container and at least one handle mounted therein or thereon, which in a removal position projects out of/from the receiving container in a manner such that it can be grasped in order to enable the sieve basket to be carried, and which in a locking position is arranged in/abutting on the receiving container, wherein the at least one handle is movable automatically, in a spring-preloaded manner, into the removal position by an automatically operating driving mechanism that comprises at least one leg spring, and the at least one handle is configured to be held in the locking position by a holding/release mechanism, which has for this purpose a holding/release element which can be manually disengaged directly or indirectly and is configured to be reached and actuated from outside of the sieve basket, and wherein in the locking position, an engagement is provided between the holding/release element and the at least one handle, the holding/release element is arranged at the sieve basket so as to be translationally movable and the sieve basket is configured such that a translational movement of the holding/release element releases the engagement between the holding/release element and the at least one handle, and when the engagement is released, the at least one handle is configured to be swiveled-out and thus to be rotationally moved from the locking position to the removal position by the at least one leg spring.

2. The sieve basket according to claim 1, wherein the receiving container has a substantially rectangular bottom, wherein a first narrow side wall, second narrow side wall, first wide sidewall and second wide sidewall extend from the bottom, wherein the at least one handle comprises a first handle and a second handle, wherein the first handle is arranged along and extends over the first narrow side wall, wherein the second handle is arranged along and extends over the second narrow side wall, and wherein the first handle and second handle are each pivotably mounted on the first and second wide side walls, respectively.

3. The sieve basket according to claim 2, wherein the first and second handles are arranged in the locking position, at least in sections substantially without slots, along the first and second narrow side walls respectively, so that a volume of an interior space of the receiving container accessible by objects is reduced only by a volume of the first and second handles.

4. The sieve basket according to claim 2, wherein each of the first and second narrow side walls has a notch or recess at its upper end side, wherein each of the first and second handles is curved outwardly in its longitudinal center portion, in such a way that a handle bracket portion thereof, which is curved outwardly, projects into one of the notches or recesses and thus substantially complements one of the first and second narrow side walls in a flush manner, wherein the handle bracket portions form part of the first and second narrow side walls in the locking position.

5. The sieve basket according to claim 1, wherein the holding/release element is a spring-preloaded, displaceable latching nose, a spring-preloaded, rotatable disk, or a pivotable clamping plate.

6. The sieve basket according to claim 1, wherein the holding/release element is a push-to-open mechanism.

7. The sieve basket according to claim 1, wherein the holding/release element is arranged substantially centrally of the at least one handle in a container width direction.

8. The sieve basket according to claim 1, wherein the sieve basket has a cover which is removable from the receiving container by actuation of a cover-release mechanism, wherein the cover-release mechanism is coupled or operatively connected to the holding/release mechanism in such a way that actuation of the cover-release mechanism simultaneously triggers actuation of the holding/release element.

9. The sieve basket according to claim 1, wherein the at least one leg spring has a degressive characteristic curve, so that a transfer from the locking position to the removal position is faster at a beginning of the transfer than at an end of the transfer.

10. The sieve basket according to claim 1, wherein the at least one leg spring is interposed between the receiving container and the at least one handle and comprises a fixed leg and a moving leg, wherein the fixed leg is coupled to the receiving container, the moving leg is connected to the at least one handle, and when the at least one handle is swiveled-out from the locking position to the removal position, the fixed leg is retained in its position and the moving leg travels away from the fixed leg.

11. The sieve basket according to claim 1, wherein the at least one leg spring is interposed between the receiving container and the at least one handle, wherein the at least one leg spring comprises a fixed leg and a moving leg, wherein the fixed leg is coupled to the receiving container and the moving leg is connected to the at least one handle, wherein the moving leg is parallel to the fixed leg when the at least one handle is in the locking position, and wherein the moving leg is non-parallel to the fixed leg when the at least one handle is in the removal position.

12. The sieve basket according to claim 11, wherein the moving leg is substantially perpendicular to the fixed leg when the at least one handle is in the removal position.

13. A sieve basket for receiving medical articles to be disinfected or sterilized, the sieve basked comprising:

a receiving container comprising a bottom wall, a first side wall, a second side wall, a first end wall and a second end wall;

a handle having a first end pivotally mounted to the first side wall, a second end pivotally mounted to the second sidewall, and a gripping portion between the first end and second end;

a drive mechanism comprising a spring interposed between the receiving container and the handle; and a holding/release element connected to one of the first end wall and second end wall, the first side wall, second side wall, first end wall and second end wall defining a top edge opposite the bottom wall, the handle being pivotable relative to the first and second sidewalls to a removal position in which the gripping portion projects above the top edge, the handle also being pivotable relative to the first and second sidewalls to a locking position in which the gripping portion is releasably engaged by the holding/release element.

14. The sieve basket according to claim 13, wherein the spring exerts a bias on the handle that urges the handle toward the removal position.

15. The sieve basket according to claim 14, wherein the handle is pivotable from the removal position toward the locking position against the bias of the spring.

16. The sieve basket according to claim 15, wherein the holding/release element releasably engages the gripping portion in the locking position to maintain the handle in the locking position against the bias of the spring.

17. The sieve basket according to claim 13, wherein the gripping portion extends through said one of the first end wall and second end wall in the locking position.

18. The sieve basket according to claim 13, wherein the holding/release element is movable between a holding position, in which the holding/release element engages the gripping portion, and a release position, in which the holding/release element is moved out of engagement with the gripping portion, the holding/release element being spring-biased toward the holding position.

* * * * *